US010169861B2

(12) United States Patent
Ozaki et al.

(10) Patent No.: US 10,169,861 B2
(45) Date of Patent: *Jan. 1, 2019

(54) IMAGE PROCESSING APPARATUS, NON-TRANSITORY COMPUTER READABLE MEDIUM, AND IMAGE PROCESSING METHOD

(71) Applicant: FUJIFILM CORPORATION, Tokyo (JP)

(72) Inventors: Ryota Ozaki, Yokohama (JP); Hideto Oda, Yokohama (JP); Noriji Kato, Yokohama (JP)

(73) Assignee: FUJIFILM CORPORATION, Tokyo (JP)

( * ) Notice: Subject to any disclaimer, the term of this patent is extended or adjusted under 35 U.S.C. 154(b) by 93 days.

This patent is subject to a terminal disclaimer.

(21) Appl. No.: 15/062,866

(22) Filed: Mar. 7, 2016

(65) Prior Publication Data

US 2016/0189378 A1 Jun. 30, 2016

Related U.S. Application Data

(63) Continuation of application No. PCT/JP2014/071596, filed on Aug. 19, 2014.

(30) Foreign Application Priority Data

Dec. 27, 2013 (JP) ................. 2013-271140

(51) Int. Cl.
*G06K 9/00* (2006.01)
*G06T 7/00* (2017.01)
(Continued)

(52) U.S. Cl.
CPC ....... *G06T 7/0012* (2013.01); *G01N 15/1468* (2013.01); *G01N 33/49* (2013.01);
(Continued)

(58) Field of Classification Search
None
See application file for complete search history.

(56) References Cited

U.S. PATENT DOCUMENTS 6,546,123 B1 4/2003 McLaren et al.
7,968,832 B2* 6/2011 Okuda .................. G01J 3/46
250/201.3

(Continued)

FOREIGN PATENT DOCUMENTS

CN 101949819 A 1/2011
CN 102411715 A 4/2012
(Continued)

OTHER PUBLICATIONS

Aug. 11, 2017 Extended Search Report issued in European Patent Application No. 14873584.8.
(Continued)

*Primary Examiner* — Nancy Bitar
(74) *Attorney, Agent, or Firm* — Oliff PLC

(57) ABSTRACT

An image processing apparatus includes a number-of-target-cells estimating unit for estimating, on the basis of a feature of a target sample, the number of target cells included in the target sample, and a detection parameter setting unit for setting, on the basis of the estimated number of target cells, a detection parameter regarding a process of detecting target cells in a captured image of the target sample.

8 Claims, 10 Drawing Sheets

(51) Int. Cl.
*G01N 15/14* (2006.01)
*G01N 33/49* (2006.01)
*G06K 9/52* (2006.01)
*G06K 9/62* (2006.01)
*G06T 7/73* (2017.01)
*C12M 1/34* (2006.01)
*G01N 15/00* (2006.01)
*G06K 9/46* (2006.01)

(52) U.S. Cl.
CPC ......... *G06K 9/00127* (2013.01); *G06K 9/52* (2013.01); *G06K 9/6267* (2013.01); *G06T 7/73* (2017.01); *C12M 41/36* (2013.01); *G01N 2015/0073* (2013.01); *G01N 2015/1486* (2013.01); *G06K 2009/4666* (2013.01); *G06T 2207/10056* (2013.01); *G06T 2207/30024* (2013.01); *G06T 2207/30242* (2013.01)

(56) References Cited

U.S. PATENT DOCUMENTS

| | | | |
|---|---|---|---|
| 9,070,005 B2 | 6/2015 | Ozaki et al. | |
| 9,296,982 B2* | 3/2016 | Kiyota | C12M 23/50 |
| 9,363,486 B2* | 6/2016 | Usuba | G06K 9/0014 |
| 9,471,977 B2* | 10/2016 | Ozaki | G02B 21/244 |
| 2002/0010618 A1 | 1/2002 | Pellegrinelli et al. | |
| 2002/0110928 A1 | 8/2002 | Yahiro | |
| 2005/0163359 A1 | 7/2005 | Murao et al. | |
| 2008/0241848 A1* | 10/2008 | Tsipouras | C12Q 1/6841 435/6.11 |
| 2008/0260206 A1 | 10/2008 | Kanda | |
| 2009/0115892 A1* | 5/2009 | Sako | H04N 1/0097 348/376 |
| 2009/0141960 A1 | 6/2009 | Yamamoto | |
| 2009/0206234 A1* | 8/2009 | Okuda | G01J 3/46 250/201.2 |
| 2010/0232674 A1 | 9/2010 | Amakawa et al. | |
| 2010/0267059 A1 | 10/2010 | Jacobson | |
| 2012/0314092 A1* | 12/2012 | Chu | G01N 15/1463 348/207.1 |
| 2013/0163844 A1* | 6/2013 | Ozaki | G06K 9/0014 382/133 |
| 2014/0092228 A1 | 4/2014 | Usuba et al. | |
| 2016/0187637 A1* | 6/2016 | Ozaki | G06K 9/00127 348/79 |

FOREIGN PATENT DOCUMENTS

| | | |
|---|---|---|
| CN | 103218804 A | 7/2013 |
| EP | 1414231 A1 | 4/2004 |
| JP | 2002-214228 A | 7/2002 |
| JP | 2003-504627 A | 2/2003 |
| JP | 2004-248619 A | 9/2004 |
| JP | 2010-216920 A | 9/2010 |
| JP | 2011-177063 A | 9/2011 |
| JP | 2012-254042 A | 12/2012 |
| JP | 2013-027368 A | 2/2013 |
| WO | 99/45385 A1 | 9/1999 |
| WO | 01/04828 A1 | 1/2001 |
| WO | 01/37012 A1 | 5/2001 |

OTHER PUBLICATIONS

Nov. 25, 2014 International Search Report issued in International Patent Application No. PCT/JP2014/071596.

Nov. 25, 2014 Written Opinion issued in International Patent Application No. PCT/JP2014/071596.

Jan. 11, 2017 Office Action issued in Chinese Patent Application No. 201480055887.2.

Yang, Xiafeng. "Relationship of the examination and proportion of embryo nucleated ery-throcyte in the material peripheral blood and gestational age." Chinese Medical Herald, vol. 9, pp. 109-112, 2012.

* cited by examiner

FIG. 3

| SAMPLE ID | SPECIMEN ID | DETECTION TARGET FLAG | NUCLEUS CANDIDATE REGION PARAMETERS | | DETERMINATION TARGET REGION PARAMETERS | | |
|---|---|---|---|---|---|---|---|
| | | | COLOR RANGE | NUMBER OF CONNECTED PIXELS | STEP WIDTH | MAXIMUM MAGNIFICATION | MAGNIFICATION LEVELS |
| U0001 | S0001 | T | 60 - 250 | 100 | 1 | 4 | 6 |
| U0001 | S0002 | T | 90 - 240 | 150 | 2 | 4 | 3 |
| U0001 | S0003 | F | 60 - 250 | 100 | 1 | 4 | 6 |
| U0002 | S0011 | T | 90 - 240 | 150 | 2 | 4 | 3 |

FIG. 4
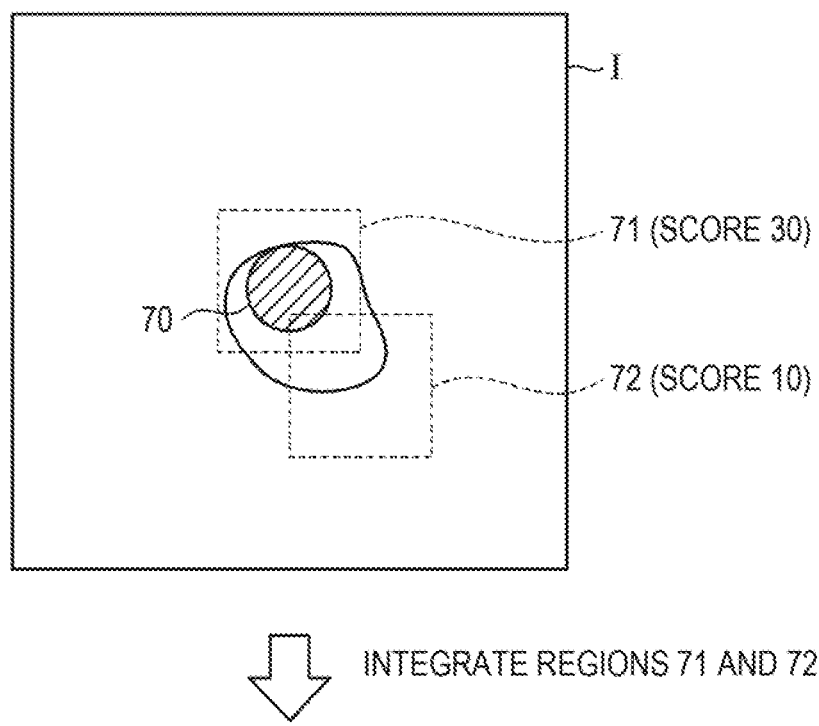
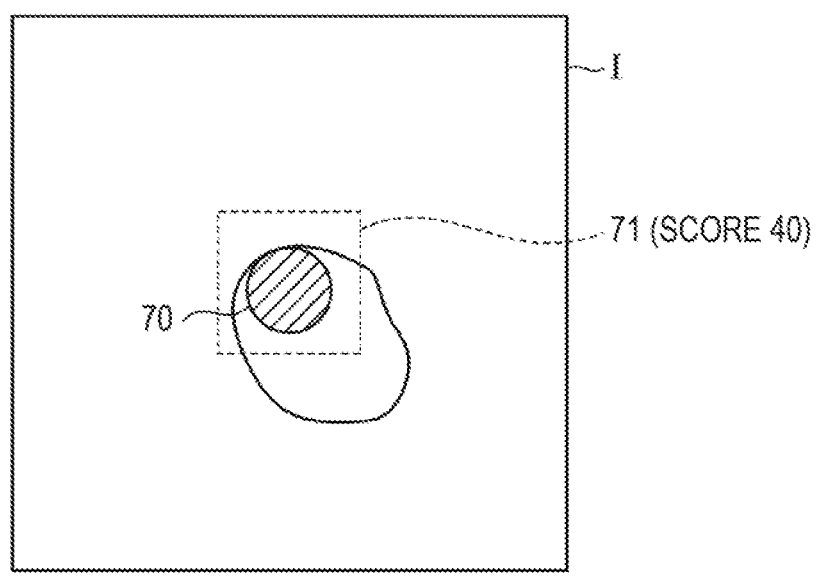

IMAGE PROCESSING APPARATUS, NON-TRANSITORY COMPUTER READABLE MEDIUM, AND IMAGE PROCESSING METHOD

CROSS REFERENCE TO RELATED APPLICATION

This is a continuation of International Application No. PCT/JP2014/1071596 filed on Aug. 19, 2014, and claims priority from Japanese Patent Application No. 2013-271140, filed on Dec. 27, 2013.

BACKGROUND

Technical Field

The present invention relates to an image processing apparatus, non-transitory computer readable medium, and an image processing method.

SUMMARY

An aspect of the present invention provides an image processing apparatus including an estimation unit that estimates, based on a feature of a target sample, a number of target cells included in the target sample; and a setting unit that sets, based on the estimated number of target cells, a detection parameter regarding a process of detecting the target cells in a captured image of the target sample.

BRIEF DESCRIPTION OF DRAWINGS

Exemplary embodiment(s) of the present invention will be described in detail based on the following figures, wherein:

FIG. 3 is a diagram illustrating an example of a detection parameter management table;

FIG. 4 is a diagram describing exemplary integration of target cell candidate regions;

DETAILED DESCRIPTION

Hereinafter, an exemplary embodiment for implementing the present invention will be described in accordance with the drawings.

[1. Description of System Configuration]

Figure 1:
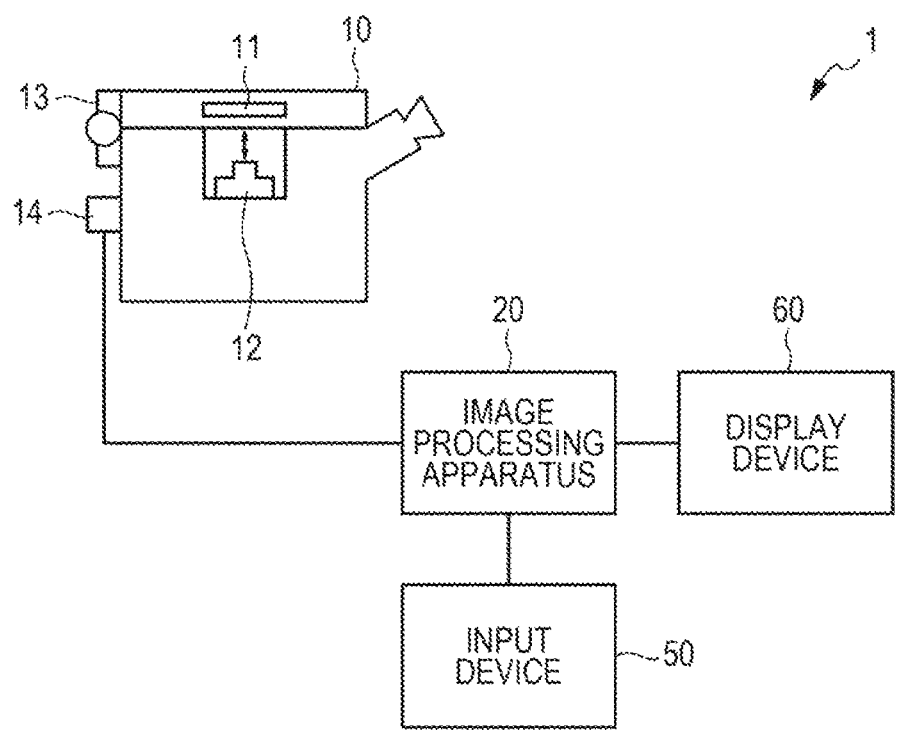
FIG. 1 is a diagram illustrating an exemplary system configuration of an image processing system according to an embodiment.

FIG. 1 illustrates an exemplary system configuration of an image processing system 1 according to the embodiment. As illustrated in FIG. 1, the image processing system 1 includes an optical microscope 10, an image processing apparatus 20, an input device 50, and a display device 60. The image processing apparatus 20 is connected to the optical microscope 10, the input device 50, and the display device 60 so as to be capable of communicating data.

The optical microscope 10 captures an image of a test object on a slide 11 placed on a stage with a CCD camera 14 via an optical system such as an objective lens(es) 12. The optical microscope 10 includes a focusing mechanism 13 that changes the distance between the slide 11 and the objective lens 12, and the optical microscope 10 is configured to capture an image of the test object on the slide 11 at different focusing distances. In the embodiment, maternal blood is applied to the slide 11, and the slide 11 is stained with May-Giemsa, which is used as a test object. This stains fetal nucleated red blood cells (NRBCs) in the maternal blood blue-purple. Hereinafter, NRBCs are referred to as target cells.

The image processing apparatus 20 obtains a captured image, captured by the optical microscope 10, and detects target cells in the obtained captured image. For example, the image processing apparatus 20 may determine a score (such as a probability) indicating the probability that target cells are included in a determination target region set in the captured image, captured by the optical microscope 10, on the basis of a discriminator that has learned conditions for discriminating target cells. Note that a process of detecting target cells, performed by the image processing apparatus 20, will be described in detail later.

The input device 50 is a device such as a keyboard or a mouse, and inputs an operation accepted from a user to the image processing apparatus 20. For example, the image processing apparatus 20 obtains information on an image region specified, regarding an image displayed on the display device 60, by the user by using the input device 50 as learning information for learning positive and negative examples of target cells, or image features of other particular cells, and may have the discriminator learn conditions (discrimination parameters) for discriminating target cells on the basis of the learning information.

The display device 60 is, for example, a liquid crystal display device 60, and displays a screen on the basis of the result of a process performed by the image processing apparatus 20. For example, the display device 60 displays a captured image captured by the optical microscope 10, the result of detecting target cells by the image processing apparatus 20, or the like.

[2. Description of Functions Included in Image Processing Apparatus 20]

Next, functions included in the image processing apparatus 20 according to the embodiment will be described.

Figure 2:
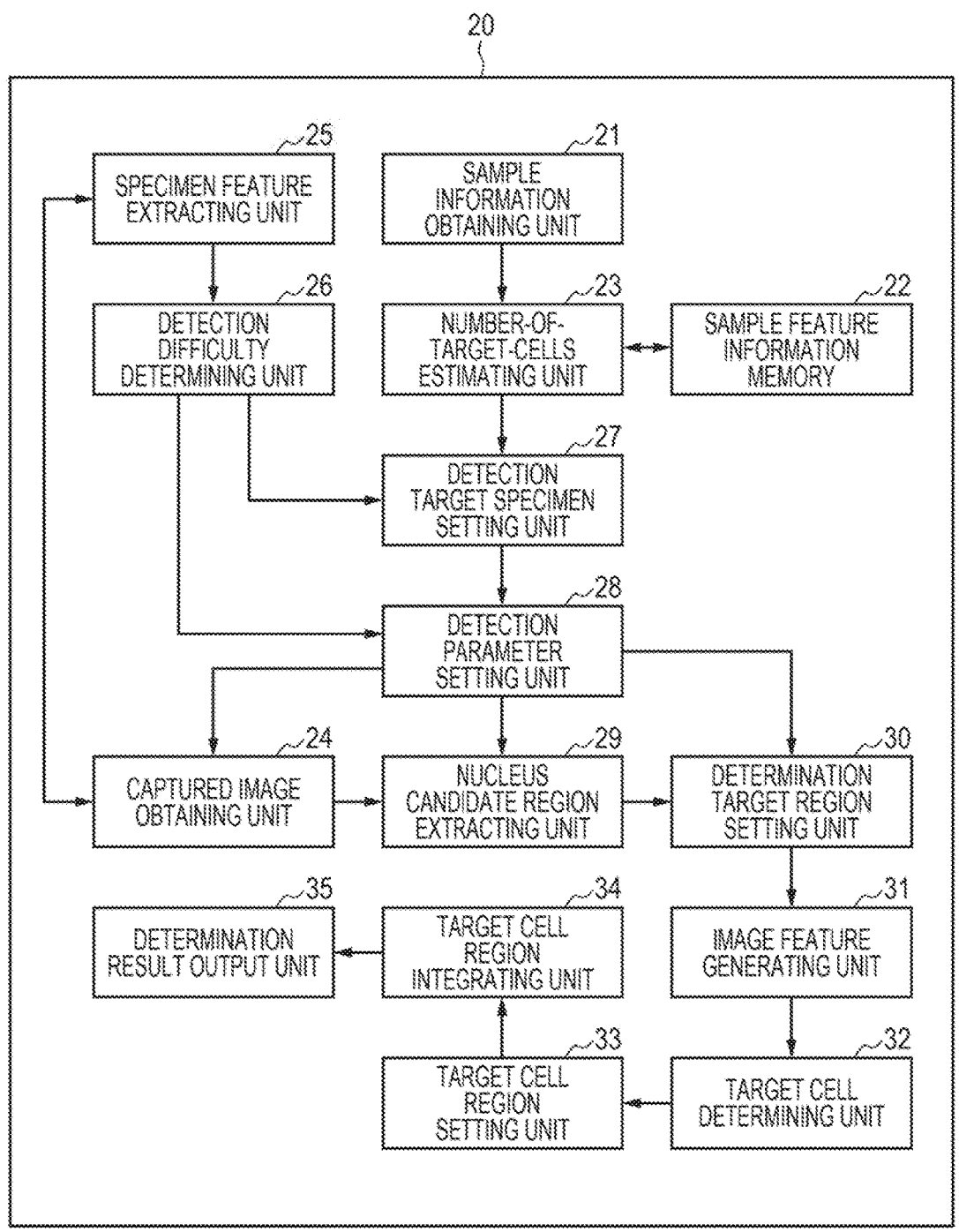
FIG. 2 is a functional block diagram illustrating an example of functions included in an image processing apparatus.

FIG. 2 is a functional block diagram illustrating an example of functions included in the image processing apparatus 20. As illustrated in FIG. 2, the image processing apparatus 20 includes a sample information obtaining unit 21, a sample feature information memory 22, a number-of-target-cells estimating unit 23, a captured image obtaining unit 24, a specimen feature extracting unit 25, a detection difficulty determining unit 26, a detection target specimen setting unit 27, a detection parameter setting unit 28, a nucleus candidate region extracting unit 29, a determination target region setting unit 30, an image feature generating unit 31, a target cell determining unit 32, a target cell region setting unit 33, a target cell region integrating unit 34, and a determination result output unit 35.

The functions of the above-mentioned units included in the image processing apparatus 20 may be realized by reading and executing a program stored in a computer-readable information storage medium, by the image processing apparatus 20, which is a computer including control means such as a CPU, storage means such as a memory, and input-output means that transmits/receives data to/from an external device. Note that the program may be supplied to the image processing apparatus 20 through an information storage medium such as an optical disk, a magnetic disk, a magnetic tape, a magneto-optical disk, or a flash memory, or may be supplied to the image processing apparatus 20 via a data communication network such as the Internet. Hereinafter, the functions of the units included in the image processing apparatus 20 will be described in detail.

The sample information obtaining unit 21 obtains information (sample information) on a sample of a test target (mother). For example, the specimen information obtaining unit 21 may obtain sample information on the basis of data input via the input device 50. For example, the sample information may include the age, medical history, weeks of pregnancy, or the like of a person (mother) from whom maternal blood as a test object has been taken.

The sample feature information memory 22 stores information for use in estimating target cells included in a sample, on the basis of a feature of the sample. For example, with respect to a category in accordance with a feature of a sample, the sample feature information memory 22 may store the number of target cells per unit blood volume according to each category, for example. For example, the image processing apparatus 20 may generate and cluster a feature vector for each sample on the basis of each item of information, that is, the age, medical history, and weeks of pregnancy, and may associatively store a pre-measured representative value (such as an average value) of the number of target cells (nucleated red blood cells) per unit blood volume for a sample belonging to each cluster, in the sample feature information memory 22. In addition, the sample feature information memory 22 may store a table or an equation defining the relationship between the age, medical history, and weeks of pregnancy with a corresponding number of nucleated red blood cells.

The number-of-target-cells estimating unit 23 estimates the number of target cells included in a sample, on the basis of sample information (information representing a feature of the sample) regarding the sample, obtained by the sample information obtaining unit 21, and information stored in the sample feature information memory 22. For example, for a category corresponding to the sample information obtained by the sample information obtaining unit 21, the number-of-target-cells estimating unit 23 estimates the number of target cells included in a test object (maternal blood) obtained from the sample, on the basis of a representative number of target cells, stored in the sample feature information memory 22. For example, for a category corresponding to the sample information obtained by the sample information obtaining unit 21, the number-of-target-cells estimating unit 23 may obtain the estimated number of target cells by multiplying the number of nucleated red blood cells per unit blood volume, stored in the sample feature information memory 22, and the blood volume of the test object.

In addition, the method of estimating the number of target cells is not limited to that described above. For example, the sample feature information memory 22 may store in advance, for one or more samples, a feature vector(s) of the sample(s) and the number of target cells in association with each another. The number-of-target-cells estimating unit 23 identifies a feature vector that is similar to a feature vector of a target sample (for example, the distance between the feature vectors is shortest) among the feature vector(s) of the sample(s), stored in the sample feature information memory 22, and may regard the number of target cells associated with the identified feature vector as the number of target cells in the target sample.

The captured image obtaining unit 24 obtains a captured image of a test object (maternal blood) on the slide, obtained from a sample. For example, the captured image obtaining unit 24 obtains, from the optical microscope 10, a captured image of a test object (maternal blood), captured with the CCD camera 14 included in the optical microscope 10. In addition, the captured image obtaining unit 24 may obtain a captured image in the case where a detection target flag defined for a target test object is true (T) on the basis of later-described detection parameters, and may not obtain a captured image in the case where a detection target flag defined for a target test object is false (F).

The specimen feature extracting unit 25 extracts features of a target specimen. Features of a specimen include information indicating a generation state of the specimen. For example, the specimen feature extracting unit 25 may extract, as specimen features, the thickness evenness of a specimen prepared from a sample, the staining intensity of the cell nucleus, the content by percentage of white blood cells, and the like. The specimen feature extracting unit 25 may extract specimen features of each of all or some of specimens (such that specimens are limited to those serving as detection targets) prepared from a target sample.

The specimen feature extracting unit 25 may calculate, for example, the thickness evenness (A) of a specimen by measuring the depth from the surface of the specimen to the slide at a plurality of points in the specimen by using the optical microscope 10, and obtaining the reciprocal of a variance of the measured depths.

The specimen feature extracting unit 25 may calculate, for example, the staining intensity (B) of the cell nucleus in a specimen as a value obtained by dividing a predetermined threshold by the average intensity value of a captured image of the specimen (may be captured with the optical microscope 10) (that is, threshold/average intensity value), or as the proportion of pixels with intensity values lower than a predetermined threshold in a captured image of the specimen.

The specimen feature extracting unit 25 may calculate, for example, the content by percentage (C) of white blood cells in a specimen as the proportion of pixels of colors that are lighter than a predetermined density in a captured image of the specimen (may be captured with the optical microscope 10).

The detection difficulty determining unit 26 determines the difficulty (Df) in detecting target cells in a specimen, on the basis of specimen features extracted by the specimen feature extracting unit 25. For example, the detection difficulty determining unit 26 may calculate the detection difficulty Df of a specimen by using the following equation (1) on the basis of the thickness evenness A of the specimen, the staining intensity B of the cell nucleus in the specimen, and the content by percentage C of white blood cells in the specimen, which are extracted by the specimen feature extracting unit 25. Note that $w1$, $w2$, and $w3$ may be predetermined coefficients that satisfy $w1+w2+w3=1$ and that are greater than or equal to 0; $A0$ may be a reference value of the thickness evenness of the specimen; $B0$ may be a reference value of the staining intensity of the cell nucleus in the specimen; and C0 may be a reference value of the content by percentage of white blood cells in the specimen.

$$Df=w1 \cdot A0/A+w2 \cdot B0/B+w3 \cdot C/C0 \quad (1)$$

According to the above-mentioned equation (the detection difficulty Df is calculated to be lower as the value of the thickness evenness A of the specimen becomes greater; the detection difficulty Df is calculated to be lower as the value of the staining intensity B of the cell nucleus in the specimen becomes greater; and the detection difficulty Df is calculated to be greater as the value of the content by percentage C of white blood cells in the specimen becomes greater. Note that the detection difficulty determining unit 26 may correct the detection difficulty Df, calculated by the above-mentioned equation (1), to take a value from 0 to 1. For example, the detection difficulty determining unit 26 may have 0 for Df when Df is less than a lower threshold and may have 1 for Df when Df is greater than an upper threshold (such as a value greater than 1).

The detection target specimen setting unit 27 sets specimens serving as detection targets from among a plurality of specimens prepared from a target sample, on the basis of at least one of the estimated number (Cb) of target cells estimated by the number-of-target-cells estimating unit 23 and the detection difficulty (Df) determined by the detection difficulty determining unit 26.

The detection target specimen setting unit 27 calculates the number of target cells per specimen (a=Cb/N) by, for example, dividing the estimated number (Cb) of target cells estimated for a target sample by the number (N) of specimens prepared from the test object. Here, when Cb>Z for the necessary number (Z) of target cells, the detection target specimen setting unit 27 determines an integer X that satisfies a·X≥Z as the number of specimens serving as detection targets, and, when Cb≤Z, the detection target specimen setting unit 27 determines the number of specimens serving as detection targets as N (all specimens). The detection target specimen setting unit 27 may select, from among N specimens prepared from the test object, specimens the number of which is equivalent to the number of specimens serving as detection targets (for example, in the order of identification number or in the order of generation date and time), and may set the detection target flags of the selected specimens to true (T) and the detection target flags of unselected specimens to false (F).

In addition, in the case of setting specimens serving as detection targets on the basis of the detection difficulty calculated by the detection, difficulty determining unit 26, the detection target specimen setting unit 27 may set, for example, among a plurality of specimens prepared from a target sample, specimens whose detection difficulties are less than or equal to a threshold as detection targets.

The detection parameter setting unit 28 sets detection parameters for use in a detection process for specimens prepared from a test object. For example, the detection parameter setting unit 28 sets detection parameters on the basis of at least one of detection target specimens set by the detection target specimen setting unit 27 and the detection difficulty determined by the detection difficulty determining unit 26. For example, the detection parameters may include a detection target flag indicating whether the specimen serves as a detection target, nucleus candidate region parameters indicating conditions of an image region extracted as a nucleus candidate region from a captured image of the specimen, and determination target region parameters indicating conditions for setting a determination target region set for a captured image of the specimen.

FIG. 3 illustrates an example of a detection parameter management table storing detection parameters set by the detection parameter setting unit 28. As illustrated in FIG. 3, the detection parameter management table associatively stores a sample ID for identifying a sample, a specimen ID for identifying each of a plurality of specimens obtained from the sample, a detection target flag indicating whether each specimen serves as a detection target, nucleus candidate region parameters, and determination target region parameters. Note that the nucleus candidate region parameters include the color range of target pixels extracted as a nucleus candidate region, and a threshold of the number of connected pixels. In addition, the determination target region parameters include a step width indicating the amount of shift between pixels serving as the base points of a determination target region in a nucleus candidate region, the maximum magnification indicating, regarding determination target regions of a plurality of sizes set for pixels serving as the base points of the determination target regions, a size ratio between the minimum determination target region and the maximum determination target region, and magnification levels indicating the number of levels of magnification executed from the minimum determination target region to the maximum determination target region.

The detection parameter setting unit 28 may set detection parameters on the basis of at least one of a margin Y, which is the difference between the product of the number X of specimens serving as detection targets and the number a of target cells per specimen, set by the detection target specimen setting unit 27, and the necessary number Z of target cells (Y=a·X−Z), and the detection difficulty Df determined by the detection difficulty determining unit 26. More specifically, the detection parameter setting unit 28 may preliminarily determine detection parameters for each of M levels (L1 to LM) (M is an integer greater than or equal to 2) (note that, for the same image, the number of nucleus candidate regions and determination target regions extracted/set in accordance with detection parameters at Li+1 is greater than the number of nucleus candidate regions and determination target regions extracted/set in accordance with detection parameters at Li), determine the level on the basis of the value of at least one of the margin Y and the detection difficulty Df, and set detection parameters on the basis of the determined level. For example, the detection parameter setting unit 28 may preliminarily define the range of the margin for each of M levels, and may determine the level on the basis of to which level's range the above-calculated Y belongs. Alternatively, for example, the detection parameter setting unit 28 may preliminarily define the range of the detection difficulty for each of M levels, and may determine the level on the basis of to which level's range the above-calculated Df belongs. Alternatively, for example, the detection parameter setting unit 28 may preliminarily define the range of the sum of the margin and the detection difficulty for each of M levels, and may determine the level on the basis of to which levers range the above-calculated sum of Y and Df belongs.

Note that the detection parameter setting unit 28 may set, for each specimen set by the detection target specimen setting unit 27, detection parameters that are different for each specimen on the basis of the detection difficulty calculated for each specimen.

The nucleus candidate region extracting unit 29 extracts, from a captured image, obtained by the captured image obtaining unit 24, of a specimen serving as a processing target, a nucleus candidate region on the basis of nucleus candidate region parameters set by the detection parameter setting unit 28 for the specimen. For example, the nucleus candidate region extracting unit 29 may perform binarization by regarding pixels included in a color range included in the nucleus candidate region parameters as black pixels and pixels not included in the color range as white pixels, and, among connected pixel groups of connected adjacent black pixels, may extract, as a nucleus candidate region, a connected pixel group having connected pixels whose number is greater than or equal to the number of connected pixels included in the nucleus candidate region parameters.

The determination target region setting unit 30 sets, for a captured image, obtained by the captured image obtaining unit 24, of a specimen serving as a processing target, a determination target region subjected to determination of whether there are target cells, on the basis of determination target region parameters set by the detection parameter setting unit 28 for the specimen and a nucleus candidate region extracted by the nucleus candidate region extracting unit 29. For example, the determination target region setting unit 30 sets, for each of one or more pixels included in a nucleus candidate region extracted by the nucleus candidate region extracting unit 29, a rectangular region around that pixel (or with reference to that pixel, which serves as a base point), as a determination target region. Here, the determination target region setting unit 30 may sequentially set determination target regions by sequentially moving, on the basis of a step width (shift amount) included in determination target region parameters set for a specimen serving as a processing target, a pixel that is in a nucleus candidate region and that serves as the base point of a determination target region, by the step width. In addition, the determination target region setting unit 30 may set, regarding a pixel serving as the base point of a determination target region, determination target regions of different sizes by changing, on the basis of the maximum magnification and the magnification levels included in the determination target region parameters set for a specimen serving as a processing target, the size of a determination target region from 1 to the maximum magnification, over the number of levels defined by the magnification levels.

The image feature generating unit 31 generates an image feature amount of a determination target region set by the determination target region setting unit 30. For example, the image feature generating unit 31 may calculate an HOG feature amount of a determination target region, and obtain the HOG feature amount as an image feature amount. Hereinafter, a process of calculating two types of HOG feature amounts will be specifically described.

The image feature generating unit 31 obtains the intensity gradient orientation and the intensity gradient magnitude at each pixel in a determination target region, splits a target image into Y blocks each having X cells, obtains a histogram of oriented gradients ([a first gradient orientation value, a second gradient orientation value, . . . , and a ninth gradient orientation value]) from the intensity gradient orientations and the intensity gradient magnitudes for each cell included in each block, and performs normalization in units of blocks so that the mean square thereof becomes 1. The image feature generating unit 31 obtains X×9, which is a value generated by combining the above-mentioned normalized histograms of oriented gradients in each block, as a feature value of that block, and obtains Y×X×9, which is a value generated by combining all the blocks in the target image, as an HOG feature amount of the determination target region.

In addition, the image feature generating unit 31 obtains the intensity gradient orientation and the intensity gradient magnitude at each pixel in a determination target region, splits a target image into Y blocks each having X cells, and obtains a histogram of oriented gradients ([a first gradient orientation value, a second gradient orientation value, . . . , and an eighteenth gradient orientation value]) from the intensity gradient orientations and the intensity gradient magnitudes for each cell included in each block. The image feature generating unit 31 obtains X×18, which is a value generated by combining the above-mentioned histograms of oriented gradients in each block, as a feature value of that block, and obtains Y×X×18, which is a value generated by combining all the blocks in the target image, as a Cell-HOG feature amount of the determination target region.

The target cell determining unit 32 determines, on the basis of the image feature amount of a determination target region, the probability (reliability) that target cells are included in the determination target region. For example, a discriminator may be caused in advance to learn conditions for discriminating target cells (discrimination parameters) on the basis of the image feature amount of an image region where target cells are shown, and the result of discriminating the image feature amount of a determination target region, obtained by the discriminator, may be obtained. Note that AdaBoost, SVM (support vector machine), or the like may be used as the discriminator. The discriminator outputs, on the basis of the image feature amount of a determination target region, a score indicating the probability (reliability) that target cells are included in the determination target region. For example, the discriminator may output a score having a positive value when cells included in a determination target region are target cells, and may output a score having a negative value when the cells are not target cells.

On the basis of the determination result obtained by the target cell determining unit 32 for a determination target region, the target cell region setting unit 33 sets a candidate, region (target cell region) including target cells. For example, the target cell region setting unit 33 may set a determination target region as a target cell candidate region when the reliability output by the discriminator is greater than or equal to 0.

The target cell region integrating unit 34 integrates, among candidate regions set by the target cell region setting unit 33, candidate regions that at least partially overlap each other into one region. For example, when a plurality of candidate regions overlap each other, the target cell region integrating unit 34 may integrate the plurality of candidate regions into one of these regions (a region with the maximum reliability, for example). Here, the target cell region integrating unit 34 may determine that a plurality of candidate regions overlap each other when these regions are determination target regions set from the same nucleus candidate region, or may determine that a plurality of candidate regions overlap each other when the plurality of candidate regions have an overlapping portion whose area is greater than or equal to a predetermined threshold. In addition, regarding the integrated candidate regions, the target cell region integrating unit 34 may leave only a candidate region with the highest reliability, or may have a region including all the overlapping candidate regions as an integrated candidate region. In addition, the target cell region integrating unit 34 may obtain the reliability of an integrated candidate region by adding the reliabilities of the candidate regions that have been integrated, or may obtain the reliability of an integrated candidate region by multiplying that reliability by the number of overlapping candidate regions.

FIG. 4 is a diagram describing exemplary integration of target cell candidate regions. As illustrated in FIG. 4, a captured image I includes a nucleus candidate region 70. For the nucleus candidate region 70, two target cell regions 71 and 72, which partially overlap each other, are set. If the score for the target cell region 71 is 30 and the score for the target cell region 72 is 10, the target cell region integrating unit 34 may integrate the target cell region 72 with the target cell region 71 whose score is maximum out of the target cell regions 71 and 72, add the score of the target cell region 72 to the score of the target cell region 71, and update the score.

The determination result output unit 35 outputs information on candidate regions integrated by the target cell region integrating unit 34 as a target cell detection result for a test object. For example, the determination result output unit 35 may display a display screen displaying candidate regions integrated by the target cell region integrating unit 34, which are sorted according to the reliability and displayed in a list, on the display device 60. Note that the determination result output unit 35 may not include a candidate region whose reliability is less than a specified or predetermined threshold in the displayed list.

[3. Exemplary Process]

Next, an exemplary process performed in the image processing system according to the embodiment will be described in detail on the basis of FIGS. 5 to 10.

[3-1. First Example]

First, a process according to a first example, executed by the image processing system 1, will be described in detail on the basis of the flowcharts illustrated in FIGS. 5 to 8.

[3-1-1(1). Main Process (1)]

Figure 5:
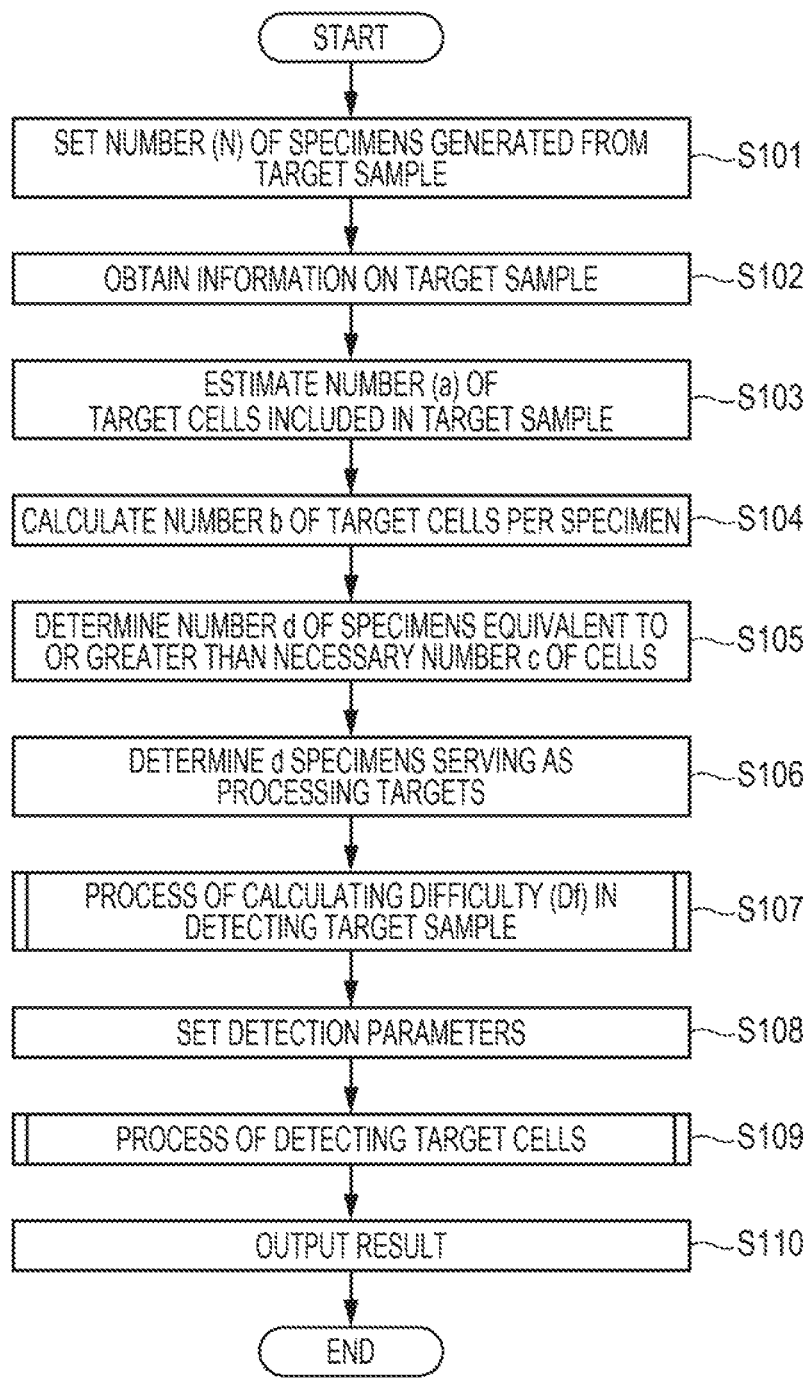
FIG. 5 is a flowchart of a process according to a first example.

As illustrated in FIG. 5, on the basis of data input from the input device 50, the image processing apparatus 20 sets the number (N (N is an integer greater than or equal to 1)) of specimens prepared from a target sample (S101), and obtains information on the target sample (sample information) (S102). Here, the sample information may include at least one of information on the age, medical history, and weeks of pregnancy.

Next, on the basis of the sample information obtained in S102, the image processing apparatus 20 estimates the number (a) of target cells included in the target sample (S103). For example, the image processing apparatus 20 may identify a category to which the sample information obtained in S102 belongs, and, on the basis of a representative number of target cells (a reference number of target cells) per unit blood, which is predetermined for the identified category, and the volume of blood of a test object serving as the specimen, may calculate the estimated number of target cells included in the sample.

On the basis of the number (a) of target cells, calculated in S103, and the number (N) of specimens, set in S101, the image processing apparatus 20 calculates the number (b) of target cells per specimen (S104). On the basis of the number (b) of target cells per specimen, calculated in S104, the image processing apparatus 20 determines the number (d) of detection target specimens equivalent to or greater than a necessary number (c) of cells needed for detection (S105).

Here, the image processing apparatus 20 selects and determines specimens serving as processing targets, the number of which is the number (d) of detection target specimens, determined in S105, from among a plurality of specimens prepared from the target sample (S106).

Next, the image processing apparatus 20 executes a process of calculating the detection difficulty indicating the difficulty in detecting target cells in each specimen serving as a processing target, determined in S106 (S107). The process of calculating the detection difficulty will be described in detail on the basis of the flowchart illustrated in FIG. 6.

[3-1-2. Process of Calculating Detection Difficulty]

Figure 6:
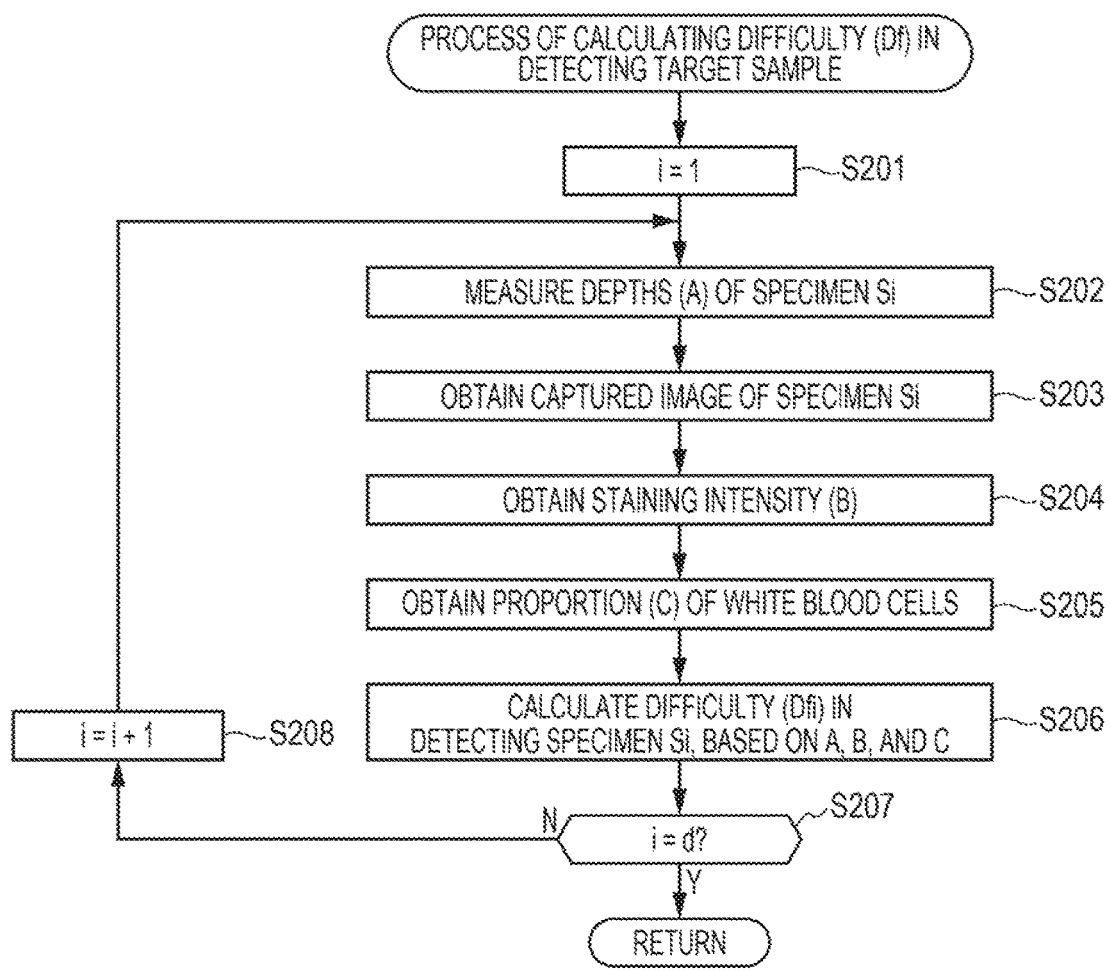
FIG. 6 is a flowchart of a process of calculating the detection difficulty.

As illustrated in FIG. 6, the image processing apparatus 20 initializes a variable i to 1 (S201), and measures depths (A) of a specimen Si (S202). For example, the depth from the surface of the specimen Si to the slide may be measured at a plurality of points in the specimen Si by using the optical microscope 10.

Next, the image processing apparatus 20 obtains a captured image of the specimen Si, captured using the optical microscope 10 (S203), and obtains the staining intensity (B) of the specimen Si on the basis of the obtained captured image (S204). For example, the image processing apparatus 20 may calculate the staining intensity (B) of the cell nucleus in the specimen Si as a value obtained by dividing a predetermined threshold by the average intensity value of the captured image of the specimen Si (that is, threshold/average intensity value), or as the proportion of pixels with intensity values lower than a predetermined threshold in the captured image of the specimen.

Further, on the basis of the captured image obtained in S203, the image processing apparatus 20 obtains the proportion (C) of white blood cells in the specimen Si (S205). For example, the image processing apparatus 20 may calculate the proportion (C) of white blood cells in the specimen Si as the proportion of pixels of colors lighter than a predetermined density in the captured image of the specimen Si.

The image processing apparatus 20 calculates the detection difficulty Df (Dfi) in detecting target cells in the specimen Si, on the basis of, for example, the above-described equation (1) and on the basis of the variance of the depths (A), the staining intensity (B) of the test object, and the proportion (C) of white blood cells (S206).

Here, when the variable i has not reached d (S207: N), the image processing apparatus 20 increments the variable i (adds 1) (S208) and returns to S202; and, when the variable i has reached d (S207: Y), the image processing apparatus 20 returns. Next, referring back to the flowchart in FIG. 5, a description will be continuously given.

[3-1-1(2). Main Process (2)]

As illustrated in FIG. 5, having finished calculating the detection difficulty Df in detecting target cells in a specimen serving as a processing target, the image processing apparatus 20 sets detection parameters on the basis of at least one of the detection difficulty Df, calculated in S107, and the information on each specimen serving as a processing target, determined in S106 (S108). For example, the detection parameters may include a detection target flag indicating whether the specimen serves as a detection target, nucleus candidate region parameters indicating conditions of an image region extracted as a nucleus candidate region from the specimen, and determination target region parameters indicating conditions for setting a determination target region set for an image of the specimen. Here, the image processing apparatus 20 may set, for example, the detection target flag on the basis of the information on each specimen serving as a processing target, determined in S106, and may set the nucleus candidate region parameters and the determination target region parameters on the basis of the detection difficulty Dfi calculated for the specimen Si.

On the basis of the detection parameters set in S108, the image processing apparatus 20 executes a process of detecting target cells in the sample (S109). The process of detecting target cells will be described in detail on the basis of the flowchart illustrated in FIG. 7.

[3-1-3. Process of Detecting Target Cells]

Figure 7:
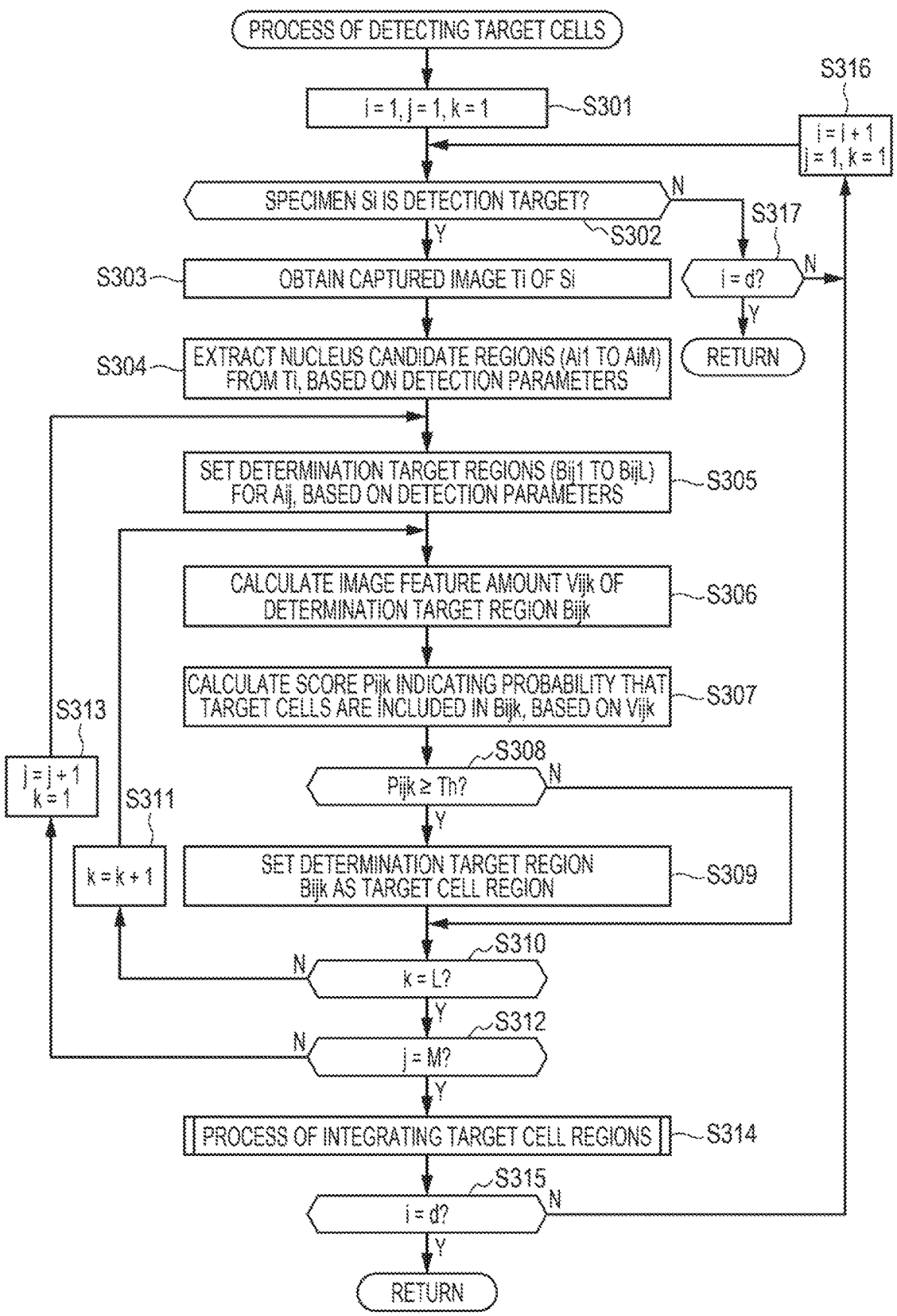
FIG. 7 is a flowchart of a process of detecting target cells.

As, illustrated in FIG. 7, the image processing apparatus 20 initializes the values of variables i, j, and k to 1 (S301), and determines whether a specimen Si of a target sample is a detection target (S302). For example, the image processing apparatus 20 may determine that the specimen Si is a detection target when the detection target flag of the specimen Si is true (T), and may determine that the specimen Si is not a detection target when the detection target flag is false (F).

When the specimen Si is a detection target (S302: Y), the image processing apparatus 20 causes, for example, the optical microscope 10 to capture an image of the specimen Si and obtains a captured image Ti of the specimen Si (S303).

Next, the image processing apparatus 20 extracts nucleus candidate regions (Ai1 to AiM) from the captured image Ti, on the basis of the nucleus candidate region parameters included in the detection parameters set for the specimen Si (S304). Note that M is the number of nucleus candidate regions included in the captured image Ti. Note that extraction of nucleus candidate regions may be executed by the above-described nucleus candidate region extracting unit 29.

The image processing apparatus 20 sets determination target regions (Bij1 to BijL) for a nucleus candidate region Aij extracted from the captured image Ti, on the basis of the determination target region parameters included in the detection parameters set for the specimen Si (S305). Note that L is the number of determination target regions set for the nucleus candidate region Aij, and setting of determination target regions may be executed by the above-described determination target region setting unit 30.

The image processing apparatus 20 calculates an image feature amount Vijk of a determination target region Bijk (S306). Note that calculation of an image feature amount may be executed by the above-described image feature generating unit 31.

On the basis of the image feature amount Vijk calculated in S306, the image processing apparatus 20 calculates a score Pijk indicating the probability that target cells are included in the determination target region Bijk (S307).

Here, when the score Pijk calculated in S307 is greater than or equal to a threshold Th (S308: Y), the image processing apparatus 20 sets the determination target region Bijk as a target cell region (S309).

After S309 or when the score Pijk calculated in S307 is less than the threshold Th (S308: N), the image processing apparatus 20 determines whether the variable k has reached L (S310), and, when the variable k has not reached L (S310: N), the image processing apparatus 20 increments k (adds 1 to k) (S311), and returns to S306. Alternatively, when the variable k has reached L in S310 (S310: Y), the image processing apparatus 20 determines whether the variable j has reached M (S312).

When the variable j has not reached M in S312 (S312: N), the image processing apparatus 20 increments j (adds 1 to j), initializes k to 1 (S313), and returns to S305. Alternatively, when the variable j has reached M in S312 (S312: Y), the image processing apparatus 20 executes a process of integrating target cell regions set for the specimen Si (S314). Here, the process of integrating target cell regions will be described in detail on the basis of the flowchart illustrated in FIG. 8.

[3-1-4. Process of Integrating Target Cell Regions]

Figure 8:
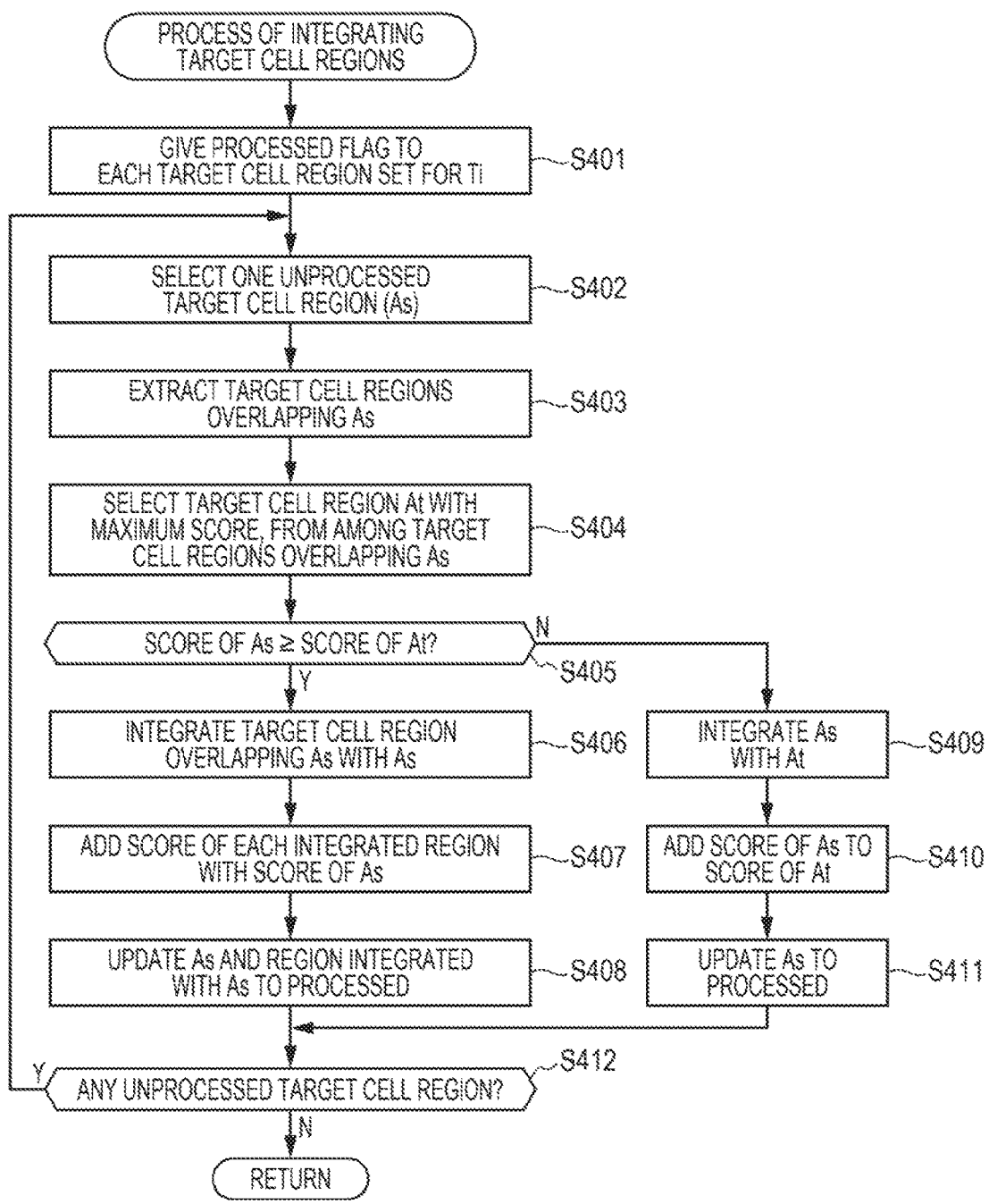
FIG. 8 is a flowchart of a process of integrating target cell regions.

As illustrated in FIG. 8, the image processing apparatus 20 gives a processed flag to each of target cell regions set for the captured image Ti of the specimen Si (S401). Note that the processed flag is a true/false value. It is assumed that processed is true (T) and unprocessed is false (F), and the initial value of the processed flag given in S401 is false (F).

Next, the image processing apparatus 20 selects one target cell region whose processed flag value indicates unprocessed (S402). Hereinafter, the target cell region selected in S402 will be referred to as As.

The image processing apparatus 20 extracts other target cell regions overlapping the target cell region As selected in S402, from among the target cell regions set for the captured image Ti (S403). The image processing apparatus 20 selects a target cell region with the maximum score from among the target cell regions extracted in S403 (S404). Hereinafter, the target cell region selected in S404 will be referred to as At.

When the score of the target cell region As is greater than or equal to the score of the target cell region At (S405: Y), the image processing apparatus 20 integrates the target cell region extracted in S403 with the target cell region As (S406), and adds the score of this other target cell region being integrated to the score of the target cell region As (S407). For example, the target cell region integrated with the target cell region As may be deleted, or the state of the target cell region integrated with the target cell region As may be updated to integrated. The image processing apparatus 20 updates the processed flag of each of the target cell region As and the other target cell region integrated with the target cell region As to true (T) (S408).

Alternatively, when the score of the target cell region As is less than the score of the target cell region At (S405: N), the image processing apparatus 20 integrates the target cell region As with the target cell region At (S409), and adds the score of the target cell region As to the score of the target cell region At (S410). The image processing apparatus 20 updates the processed flag of the target cell region As to true (T) (S411).

When there remains an unprocessed target cell region after S408 or S411 (S412: Y), the image processing apparatus 20 returns to S402. When there remains no unprocessed target cell region (S412: N), the image processing apparatus 20 ends the process of integrating target cell regions, and returns.

Here, referring back to FIG. 7, a description will be continuously given. Having finished the process of integrating target cell regions set for the specimen Si, when the variable i has not reached d (the number of detection target specimens or the number of all specimens) (S315: N), the image processing apparatus 20 increments (adds 1), initializes j and k to 1 (S316), and returns to S302. Alternatively, when the variable i has reached d in S315 (S315: Y), the image processing apparatus 20 returns.

Alternatively, when the specimen Si is not a detection target in S302 (S302: N) and the variable i has not reached d (S317: N), the image processing apparatus 20 increments i (adds 1), initializes j and k to 1 (S316), and returns to S302; and, when the variable i has reached d (S317: Y), the image processing apparatus 20 returns.

[3-1-1(3). Main Process (3)]

Here, referring back to the flowchart in FIG. 5, a description will be continuously given. Having finished the process of detecting target cells in each sample serving as a processing target, the image processing apparatus 20 outputs, on the basis of integrated target cell regions for each sample, information on the target cell regions (S110), and ends the process. For example, for each sample, the image processing apparatus 20 may sort the integrated target cell regions in descending order of the score of the target cell regions, and may display the sorted target cell regions on the display device 60.

According to the process according to the above-described first example, parameters for use in a detection process can be set on the basis of the estimated number of target cells included in a sample serving as a processing target, and the difficulty in detecting target cells in the sample serving as a processing target.

[3-2. Second Example]

Next, on the basis of the flowchart illustrated in FIG. 9, a process according to a second example, executed by the image processing system 1, will be described in detail. The second example is different from the first example in the point that detection parameters are set without using the detection difficulty.

Figure 9:
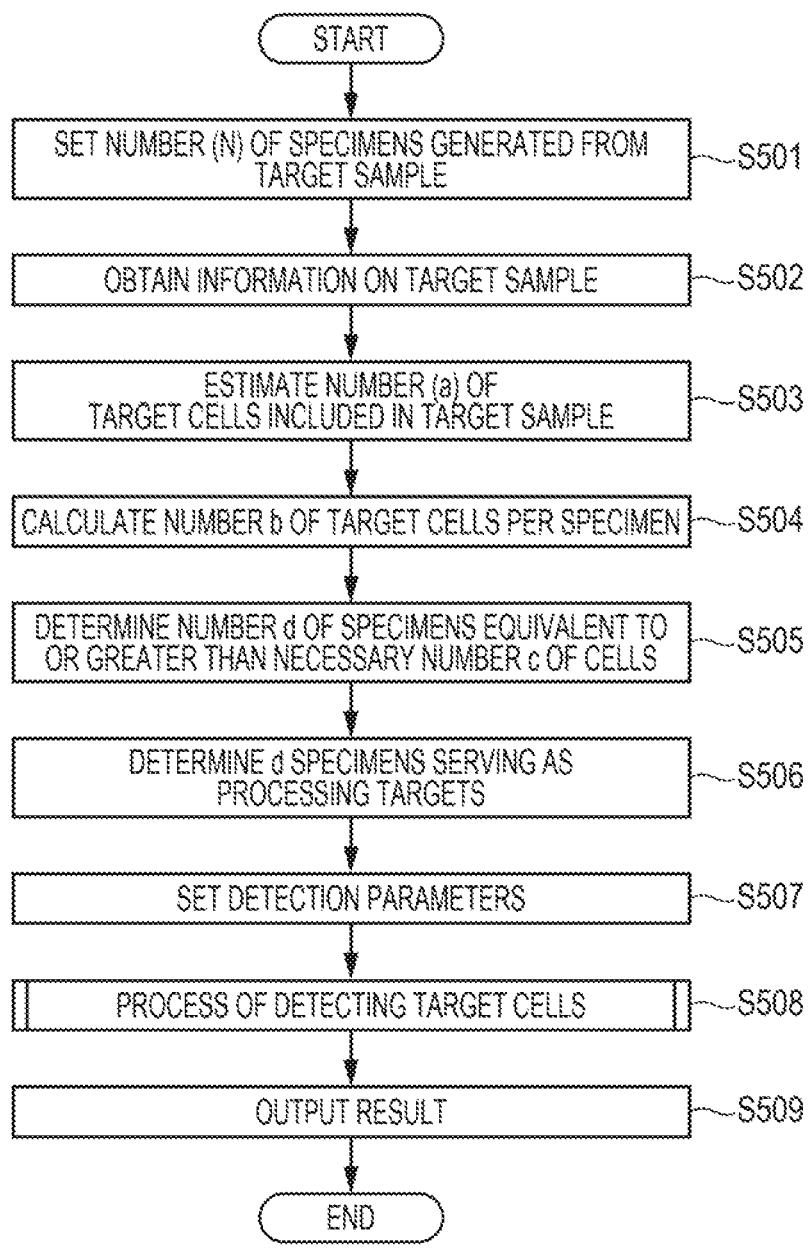
FIG. 9 is a flowchart of a process according to a second example.

As illustrated in FIG. 9, on the basis of data input from the input device 50, the image processing apparatus 20 sets the number (N (N is an integer greater than or equal to 1)) of specimens prepared from a target sample (S501), and obtains information on the target sample (sample information) (S502). Here, the sample information may include at least one of information on the age, medical history, and weeks of pregnancy.

Next, on the basis of the sample information obtained in S502, the image processing apparatus 20 estimates the number (a) of target cells included in the target sample (S503). For example, the image processing apparatus 20 may identify a category to which the sample information obtained in S502 belongs, and, on the basis of a representative number of target cells per unit blood, which is predetermined for the identified category, and the volume of blood of a test object serving as a specimen, may calculate the estimated number of target cells included in the sample.

On the basis of the number (a) of target cells, calculated in S503, and the number (N) of specimens, set in S501, the image processing apparatus 20 calculates the number (b) of target cells per specimen (S504). On the basis of the number (b) of target cells per specimen, calculated in S504, the image processing apparatus 20 determines the number (d) of detection target specimens equivalent to or greater than a necessary number (c) of cells needed for detection (S505).

Here, the image processing apparatus 20 selects and determines specimens serving as processing targets, the number of which is the number (d) of detection target specimens, determined in S505, from among a plurality of specimens prepared from the target sample (S506).

Next, the image processing apparatus 20 sets detection parameters on the basis of information on each of the specimens serving as processing targets, determined in S506, and the number (b) of target cells per specimen, calculated in S504 (S507). For example, the detection parameters may include a detection target flag indicating whether the specimen serves as a detection target, nucleus candidate region parameters indicating conditions of an image region extracted as a nucleus candidate region from the specimen, and determination target region parameters indicating conditions for setting a determination target region set for an image of the specimen. Here, the image processing apparatus 20 may set, for example, the detection target flag on the basis of the information on each specimen serving as a processing target, determined in S506, and may set the nucleus candidate region parameters and the determination target region parameters on the basis of a margin (b·d−c) obtained by subtracting the necessary number (c) of cells from b·d, which is multiplication of the number (d) of detection target specimens and the number (c) of target cells per specimen.

On the basis of the detection parameters set in S507, the image processing apparatus 20 executes a process of detecting target cells in the sample (S508). The process of detecting target cells is as illustrated in the flowchart illustrated in FIG. 7 and is common to the first example, a description of which will be omitted here.

Having finished the process of detecting target cells in each sample serving as a processing target, the image processing apparatus 20 outputs, on the basis of integrated target cell regions for each sample, information on the target cell regions (S509), and ends the process.

According to the process according to the above-described second example, parameters for use in a detection process can be set on the basis of the estimated number of target cells included in a sample serving as a processing target.

[3-3. Third Example]

Next, on the basis of the flowchart illustrated in FIG. 10, a process according to a third example, executed by the image processing system 1, will be described in detail. The third example is different from the first example in the point that detection parameters are set without using the number of target cells, which is estimated for a target sample.

Figure 10:
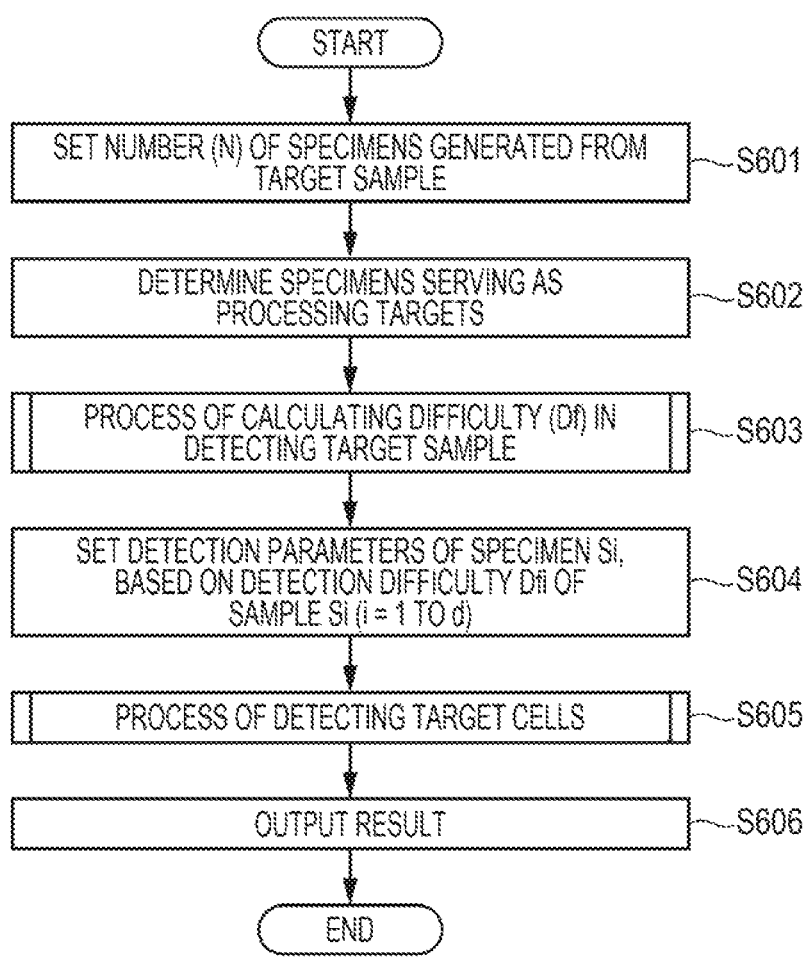
FIG. 10 is a flowchart of a process according to a third example.

As illustrated in FIG. 10, on the basis of data input from the input device 50, the image processing apparatus 20 sets the number (N (N is an integer greater than or equal to 1)) of specimens prepared from a target sample (S601).

Here, the image processing apparatus 20 determines specimens serving as processing targets, from among a plurality of specimens prepared from the target sample (S602). For example, the image processing apparatus 20 may regard all the specimens prepared from the target sample as processing targets, or may determine specimens serving as processing targets on the basis of the detection difficulty Df calculated for the target sample. For example, the image processing apparatus 20 may define a proportion in accordance with the range of the detection difficulty (specifically, the higher the detection difficulty, the higher the proportion), determines the number of specimens serving as processing targets on the basis of the product of a proportion corresponding to the detection difficulty Df and the number of all the specimens (specifically, the obtained product may be made an integer by rounding up), and determines specimens serving as processing targets on the basis of the determined number of specimens. Here, the number of specimens serving as processing targets is represented as d.

Next, the image processing apparatus 20 executes a process of calculating the detection difficulty indicating the difficulty in detecting target cells in each specimen serving as a processing target (S603). The process of detecting target cells is as illustrated in the flowchart illustrated in FIG. 6 and is common to the first example, a description of which will be omitted here.

Next, for the specimen Si (i=1 to d) serving as a processing target, the image processing apparatus 20 sets detection parameters of the specimen Si on the basis of the detection difficulty Dfi calculated in S603. For example, the detection parameters may include a detection target flag indicating whether the specimen serves as a detection target, nucleus candidate region parameters indicating conditions of an image region extracted as a nucleus candidate region from the specimen, and determination target region parameters indicating conditions for setting a determination target region set for an image of the specimen. Here, the image processing apparatus 20 may set, for example, the detection target flag on the basis of the information on each specimen serving as a processing target, determined in S603, and may set the nucleus candidate region parameters and the determination target region parameters on the basis of the detection difficulty Dfi calculated for the specimen Si.

On the basis of the detection parameters set in S604, the image processing apparatus 20 executes a process of detecting target cells in the sample (S605). The process of detecting target cells is as illustrated in the flowchart illustrated in FIG. 7 and is common to the first example, a description of which will be omitted here.

Having finished the process of detecting target cells in each sample serving as a processing target, the image processing apparatus 20 outputs, on the basis of integrated target cell regions for each sample, information on the target cell regions (S606), and ends the process.

According to the process according to the above-described third example, parameters for use in a detection process can be set on the basis of the difficulty in detecting target cells in a sample serving as a processing target.

The present invention is not construed as being limited to the above-described embodiment. For example, there is no problem in displaying target cell regions in order of score without integrating the target cell regions. In addition, the image processing apparatus 20 is not construed as being limited to a case of obtaining a captured image of a sample from the optical microscope 10, and the image processing apparatus 20 may obtain a captured image of a sample from another computer.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An image processing apparatus comprising: at least one processor that; estimates based on a feature of a target sample, a number of target cells included in the target sample; sets based on the estimated number of target cells; a detection parameter including information defining whether each of a plurality of specimens prepared from the target sample serves as a detection target of detecting whether the target cells are included; and determines, for a captured image of a specimen serving as a detection target based on the detection parameter, whether the target cells are included in a determination target region set based on the detection parameter; decides on a number of specimens including target cells, a number of which is greater than or equal to a predetermined threshold, based on the number of target cells, estimated by the at least one processor, and a number of target cells per specimen, calculated based on a number of a plurality of specimens prepared from the target sample; and selects specimens, a number of which is decided by the at least one processor, from among the plurality of specimens, wherein the at least one processor sets the detection parameter based on information on the specimens.

2. The image processing apparatus according to claim 1, wherein the at least one processor sets the setting condition such that more determination target regions are set as a difference of the threshold with respect to a product of the number of specimens, decided by the at least one processor and the calculated number of target cells per specimen is smaller.

3. The image processing apparatus according to claim 1, wherein the at least one processor further:
calculates detection difficulty indicating difficulty in detecting a number of target cells included in the specimen, based on a thickness of the specimen, an intensity of the specimen, and a density of the specimen,
wherein the at least one processor sets the detection parameter based on the calculated detection difficulty.

4. The image processing apparatus according to claim 3, wherein the at least one processor sets the setting condition such that more determination target regions are set as the detection difficulty is higher.

5. The image processing apparatus according to claim 3, wherein the at least one processor calculates the detection difficulty to be lower as thickness evenness of the specimen is higher, calculates the detection difficulty to be lower as an intensity of a nucleus included in the specimen is lower, and calculates the detection difficulty to be higher as a proportion of pixels included in the specimen that are lighter than a predetermined density is higher.

6. The image processing apparatus according to claim 1, wherein the at least one processor further integrates, in a case where there is a plurality of determination target regions that at least partially overlap each other and that are determined to include the target cells, the plurality of determination target regions with a determination target region determined by the at least one processor to be most likely to include the target cells.

7. The image processing apparatus according to claim 1, wherein the sample is maternal blood,
wherein the target cells are nucleated red blood cell,
the feature of the sample includes at least one of age, medical history, and weeks of pregnancy of a mother,
a reference number of nucleated red blood cells per unit blood volume is defined for each category based on the feature of the specimen, and
the at least one processor estimates a number of nucleated red blood cells included in the target sample, based on a reference number of nucleated red blood cells, defined for a category in accordance with the feature of the target sample, and a volume of blood of the target sample.

8. A non-transitory computer readable medium storing a program causing at least one processor estimate, based on a feature of a target sample, a number of target cells included in the target sample; set, based on the estimated number of target cells, a detection parameter including information defining whether each of a plurality of specimens prepared from the target sample serves as a detection target of detecting whether the target cells are included; and determine, for a captured image of a specimen serving as a detection target based on the detection parameter, whether the target cells are included in a determination target region set based on the detection parameter: decides on a number of specimens including target cells, a number of which is greater than or equal to a predetermined threshold, based on the number of target cells, estimated by the at least one processor, and a number of target cells per specimen, calculated based on a number of a plurality of specimens prepared from the target sample; and selects specimens, a number of which is decided by the at least one processor, from among the plurality of specimens, wherein the at least one processor sets the detection parameter based on information on the specimens.

* * * * *